United States Patent [19]

Jennings et al.

[11] Patent Number: 5,057,616
[45] Date of Patent: Oct. 15, 1991

[54] PODOPHYLLOTOXIN PURIFICATION PROCESS

[75] Inventors: Rex A. Jennings, Holland, Mich.; Jay F. Stearns, Santa Rosa, Calif.

[73] Assignee: Oclassen Pharmaceuticals, Inc., San Rafael, Calif.

[21] Appl. No.: 415,170

[22] Filed: Sep. 29, 1989

[51] Int. Cl.$^5$ ............................................. C07D 307/77
[52] U.S. Cl. .................................................... 549/298
[58] Field of Search ....................... 546/139, 152, 270; 549/298

[56] References Cited

FOREIGN PATENT DOCUMENTS 197219 10/1986 European Pat. Off. .

OTHER PUBLICATIONS

J. L. Hartwell et al., J. Chem. Soc., 72:245 (1950) (copy not included herewith as reference was included in Applicant's Description of Background Information, p. 2).

Primary Examiner—Mary C. Lee
Assistant Examiner—Peter Davis
Attorney, Agent, or Firm—Irell & Manella

[57] ABSTRACT

Podophyllotoxin is recovered from podophyllum resin with improved efficiency by adsorbing impurities out of a solution using a solid adsorbent, preferably alumina. This improvement finds application in an overall process for purifying podophyllotoxin from podophyllum resin in which the podophyllotoxin is first crystallized from the podophyllum resin, the crystals so formed are dissolved and subjected to the solid adsorbent treatment, crystals are then recovered and optionally recrystallized and dried to give the desired product.

25 Claims, No Drawings

PODOPHYLLOTOXIN PURIFICATION PROCESS

BACKGROUND OF THE INVENTION

1. Field of the Invention

This invention concerns an improved process for isolating podophyllotoxin from crude preparations containing podophyllotoxin in combination with closely related analogs.

2. Description of Background Information

Podophyllotoxin is a well known and well characterized lignan. Two major review articles which describe its early isolation and characterization are PROGRESS IN THE CHEMISTRY OF ORGANIC NATURAL PRODUCTS, L. Zechmeister, ed., Springer Verlag, Vienna, 1958, "The Chemistry of Podophyllum," pp. 84–166; and Chemical Reviews 55:957–1068, "The Naturally Occurring Lignans," W.M. Hearon et al. These works describe how, in the late nineteenth century and early in this century, a number of studies show that resins obtained from American May apples (Podophyllum, pellatum L. (American podophyllum) contain a collection of interesting, structurally related, polycyclic lignan compounds, including podophyllotoxin, quercetin, and the like. See, for example, F.A. Thompson, Am. J. Pharm., 62:245 (1890); J.C. Umney, Pharm. J., 23:207 (1892); W.R. Dunstan et al., J. Chem. Soc., 73:209 (1898); W. Bosche et al., Ann., 494:126 (1932); and Spath et al., Ber., 65:1536 (1932).

With the passage of time, other plant sources of podophyllotoxin have been identified. Other studies have focused on the composition of the crude resins and have looked at the relationships existing among the numerous components. These studies have identified materials known as alpha- and beta-peltatin (J.L. Hartwell et al., J. Chem. Soc., 72:245 (1950)), demethylpodophyllotoxin, picropodophyllin, and picropodophylloglucoside (Nadkarni et al., J. Am. Chem. Soc. 75:1308 (1953)).

Much of the interest in podophyllotoxin and the crude podophyllum resin from which it is obtained stems from its long-recognized pharmacologic activity. The podophyllum resin is famous as an ancient American indian remedy with suggested uses for abnormal skin growth conditions such as warts and the like. Some of these uses were more formalized. For example, in 1942 crude podophyllum resin was suggested as a treatment of condyloma acuminatum, a type of venereal wart, by Kaplan, I.W., New Orleans Med. Surg. J. 94:388 (1942). Podophyllum resin has also been proposed for use in a wide range of skin diseases due to infectious agents, nonspecific dermatosises, metabolic diseases, benign growths, and malignant growths. In addition, the composition of crude podophyllum resin has been further reviewed to point out that, in addition to podophyllotoxin, the alpha- and beta-peltatins, and demethylpodophyllotoxin, it contains other materials such as desoxypodophyllotoxin, H. podophyllotoxinglucoside, H. picropodophyllinglucoside, alpha-peltatinglucoside, beta-peltatinglucoside, 4,-demethylpodophyllotoxinglucoside, dehydropodophyllotoxin, sikkimotoxin, quercetin, isormamnetin, quercetin-3-galactoside, and kaempferol. These compounds are all similar to each other in ring structure and the like. However, it is generally believed that podophyllotoxin itself is the most active, and therefore most desired, species.

This focus on podophyllotoxin has led to a great interest in obtaining it in a pure form. Certain characteristics of the mixture of compounds renders this difficult. For one, podophyllotoxin isomerizes to picropodophyllin when contacted with alkali. This isomerization is favored thermodynamically and therefore is not reversible. Picropodophyllin is inactive. Purification is further complicated by the close relationship of the many compounds.

Classic methods for isolation of podophyllotoxin have involved extraction followed by laborious purification (see, e.g., Borsche, Ann., noted above, Chem. Abstracts 26:3509 (1932); Dunstan, F.L., J. Chem. Soc., noted above; and Kursten, R., Arch. Pharm. 229:220–248 (1891)). In 1950 Hartwell and Detty (J. Am. Chem. Soc. 72:246 (1950)) disclosed processes in which podophyllum resin is extracted into chloroform, leaving a dark insoluble residue amounting to about 37%, or in which podophyllotoxin is precipitated from a solution of podophyllin in alcohol. The crude podophyllotoxin so isolated is then purified by chromatography on a column of alumina. In this chromatography this crude mixture is placed on the top of the column and eluted with alcohol benzene. Fractions are taken with the podophyllotoxin eluting earlier than beta- and alpha-peltatin. In this process, however, the beta-peltatin does elute directly after the podophyllotoxin, and the alpha-peltatin is eluted by a change in solvent.

Another method for purifying podophyllotoxin is shown in U.S. Pat. No. 4,680,399, entitled PROCESS FOR THE ISOLATION AND PURIFICATION OF PODOPHYLLOTOXIN. This patent focuses on the use of nonbenzene materials for a fractional crystallization and the use of base to remove impurities.

While each of these processes has been used in the past, they are not without their limitations, not the least of which has been low efficiencies which give rise to a relatively high cost to the podophyllotoxin itself. It is an object of this invention to provide a method for recovering podophyllotoxin from podophyllum resin which is of high efficiency and low cost.

STATEMENT OF THE INVENTION

It has now been found that podophyllotoxin can be recovered with improved efficiency from podophyllin resin by adsorbing impurities out of an impure solution onto a solid adsorbent phase and thereafter recovering podophyllotoxin from the solution.

Thus, in one aspect this invention provides a podophyllotoxin purification process which has been improved by adding the above-described adsorption step.

In another aspect the invention provides an overall process for isolating podophyllotoxin from podophyllum resin. This process includes a. dissolving podophyllum resin in a lower alcohol or like solvent to yield an impure solution, b. adding an aromatic cosolvent and water to the impure solution to cause precipitation of a first stage podophyllotoxin product, c. recovering the precipitated first stage podophyllotoxin product d. dissolving the first stage podophyllotoxin product in an organic liquid phase to yield a first stage podophyllotoxin product solution, e. contacting the first stage podophyllotoxin product solution with a high surface area inorganic adsorption solid phase, thereby causing impurities present in the first stage podophyllotoxin product solution (in particular demethylpodopyllotoxin to be adsorbed onto the surface of the solid phase and yield a second stage solution of partially purified podophyllotoxin; and f. recovering the purified solid podophyllotoxin from the second stage solution.

This purified material is of a proper purity but, in preferred aspects, can be converted to a more preferred higher melting crystal form by the additional steps of g. dissolving the purified solid podophyllotoxin in a lower alcohol or like solvent to give a third stage solution, and h. recovering recrystallized podophyllotoxin as a solid from the third stage solution.

In other aspects, the invention carries out the process with the addition of acid along with the cosolvent and water addition to step b. and also can involve the addition of aqueous acid during the recrystallization of step h.

DETAILED DESCRIPTION OF THE INVENTION

The Solid Adsorbant

A key element of the process of this invention is the use of a solid adsorbent to remove impurities from a solution containing podophyllotoxin. The solid adsorbent is a particulate solid inorganic material having a high surface area, that is a surface area of at least about 0.5 square meters per gram and especially of about 1 to about 500 square meters per gram. The material employed should not be strongly basic. Strongly basic adsorbents may lead to isomerization. Preferred materials are acidic or neutral with neutral materials being more preferred. Typical materials are refractories such as boria, titania and alumina. We have had best results with alumina. Silica gel has not worked as well in our hands. Ion exchange resins do not appear to work well either.

In practice, the solid adsorbent is mixed with the solution of impure podophyllotoxin to adsorb impurities therefrom. This admixing can occur by slurrying the solid adsorbent in the solution or alternatively, a packed bed of the adsorbent can be used and the solution passed through it.

We have found that weight ratios of adsorbent to crude podophyllotoxin in the range of from about 0.5 to 1 to about 5 to 1 are useful with ratios of from about 1 to 1 to about 3 to 1 being preferred.

The length of time the adsorbent is in contact with the solution does not appear to be critical so long as it is longer than a minute or so. Typically the times necessary to suspend the material in the solution and then remove it are adequate for the adsorbant to remove the undesired impurities. Thus, typical contact times range from one or two minutes up to several hours. More preferred times range from about 5 minutes to about 45 minutes. Longer times could be used, if desired, but should be checked before using to minimize any generation of impurities or the like based on long exposures of solutions of the impure podophyllotoxin mixture to ambient conditions.

Following the contacting, the solid adsorbent is removed. This can be done by centrifugation, filtration or the like.

The Overall Process

The overall process for purifying podophyllotoxin from crude podophyllum resin is a multistep process. In the first three steps crude podophyllotoxin is recovered by crystallization from commercial podophyllum resin. This portion of the process is generally carried out by first dissolving the resin in a solvent, typically a lower alcohol such as a 1 to 3 carbon alkanol, i.e. methanol, ethanol or isopropanol. Ethanol is the preferred solvent for the crude resin. Other materials capable of dissolving the crude resin can be used as well. In general, this initial dissolving is carried out in the absence of added water. The amount of solvent to be used should be as small an amount as will totally dissolve the crude resin. Use levels in the range of 1 to about 5 liters and especially from about 2 to about 3.5 liters per kilogram of resin give good results. The crude resin is dissolved in the solvent. The mixture may be heated such as to temperatures in the range of from about 30° C. to about 100° C. to facilitate the dissolution. Mixing also can be used.

In the next step the podophyllotoxin is caused to precipitate from the solution. This can be carried out by adding a cosolvent to the solution to cause precipitation. In this case, cosolvents are usually nonpolar organics such as nonpolar hydrocarbons, for example aromatic hydrocarbons such as benzene, toluene and the like, and aliphatic hydrocarbons such as hexane, cyclohexane and the like. Petroleum distillate fractions could be used as well as a cost-saving measure. Benzene is a preferred cosolvent. Typically, water is added to the cosolvent system, as well. The amount of cosolvent is from about 0.20 parts to about 1 part based on the volume of the lower alcohol or the like solvent present. If, as is preferred, water is added, it is present in an amount ranging from about 0 parts to about 1 part based on the volume of the lower alcohol or the like solvent present and preferably from about 0.20 parts to about 1 part based on the volume of the lower alcohol or the like solvent present.

The addition of cosolvent and water is generally carried out with heating and stirring as above. It is also advantageous to acidify the mixture at this time. The amount of acid present preferably should be at least about 0.1 molar based on the total solution. Usually the acid is added with the water. This addition of acid enhances stability of the podophyllotoxin and prevents its conversion to undesired byproducts. Useful acids include organic acids such as acetic acid, propionic acid or the like. Inorganic acids can be used if desired. Acetic acid is a very good material since it is volatile and can be vaporized from the product. The upper limit on acid concentrations appears to be 0.5 molar with levels in the range from about 0.02 to about 0.25 molar being preferred. These acid levels are based on the total volume of lower alkanol, water and cosolvent present.

The addition of the water (e.g. aqueous acid) and cosolvent causes a crop of crystals to form. These are recovered by conventional centrifugation or filtration methods. To enhance the yield of crystals, the mixture is preferably cooled and allowed to stand. For reasons not wholly understood, it has been observed that during this crystallization, after a first crop is taken, if the mother liquor is allowed to stand with cooling, a second crop generally forms and can be recovered. The solids so formed are washed with a suitable liquid. Lower alcohols, and lower alcohols in combination with water and nonpolar cosolvents are good wash liquids. A final wash with ether also is effective. The washed crystals are then dried to remove wash solvent.

The next step of the process is the adsorbtion step. In this step the washed and dried crystals are first dissolved in a solvent. This solvent is typically a halohydrocarbon liquid but preferably is a mixture which includes some polar aprotic liquid such as a carbonyl group containing liquid, for example a ketone, an ester or an amide, as well as the halohydrocarbon. This polar aprotic solvent component enhances the solubility of the podophyllotoxin. Of the halohydrocarbons, chloroform, methylene chloride, dichloroethane and the like may be used. Methylene chloride gives a good balance of solvent properties and is easily removed by evaporation. As the polar aprotic solvent component one can use a ketone of up to about 6 total carbon atoms such as acetone, methylethylketone, diethylketone and the like; a lower alkyl ester of a lower carboxylic acid so as to have a total of up to about 7 carbon atoms, such as ethyl acetate or ethyl propionate; or an aliphatic amide having up to about 6 carbon atoms such as dimethylformamide. Ketones give very good results and acetone is the preferred ketone. If desired, one can use mixtures of halohydrocarbons and/or mixtures of polar aprotic solvents. The amount of solvent used should be as small as possible. Liquid levels of about 5 to about 20 parts of liquid per part of crystals can be used. Good results are obtained when the total amount of liquid is from about 15 to about 8 times of the amount of crystals. The volume ratio of halohydrocarbon to polar aprotic solvent can be from about 7 to 1 to about 2 to 1, more preferably from about 5 to 1 to about 3 to 1. Larger amounts of liquid can be used during this step but if added will increase the cost of the processing by increasing the amount of solvent to be stripped in later steps. For this reason they should generally be avoided. The contacting with the solid adsorbent is carried out at low temperature or at ambient temperature, that is from about 0° C. to about 40° C. Higher temperatures could be used but might lead to degradation of the product or poor selectivity of the adsorbant. Other process conditions are as set forth in the section describing the adsorbent material.

Following the adsorption of impurities onto the solid, the solution is separated from the solids such as by filtration, centrifugation or the like. The solids are washed, typically with a halohydrocarbon/polar aprotic solvent mixture and the washes are combined with the filtrate.

It has been observed that if the solution is allowed to stand, such as overnight, a very fine difficultly-filtrable precipitate settles out. The exact nature of this precipitate is unknown but at the present time it is isolated and removed prior to further processing.

Thereafter, the solvent is removed by evaporation. After the solid formed, and is dried, it is advantageous to redissolve it in solvent and recrystallize the material. A typical solvent for redissolving is a ketone/ether mixture although other materials may be used. This material can be evaporated to give rise to crystals which are then collected and washed with a suitable solvent such as ether. The crystals so formed may be freed of wash solution by drying or the like. The product so formed is of high purity as confirmed by analytical methods. However, because of its crystal form it may have a somewhat low melting point. The melting point can be raised by achieving a more desirable crystal structure using the following additional process steps.

The first of these additional steps is to take the pure solid obtained in the preceding step and dissolve it in a lower alcohol or other similar polar protic organic solvent, preferably containing water and acid. The water use levels and acid additions are similar to the water levels and acid addition in the first crystallization, that is from about 0.25 to about 0.75 parts of water per part of lower alcohol and acid levels ranging from about 0.02 to about 0.25 molar. Again, any removeable acid can be used but acetic acid is a very good material since it is volatile and can be vaporized from the product. The amount of solvent is the minimum which allows total dissolution of the crystals. Crystallization is effected by cooling this mixture such as to below 0° C., and especially to below −20° C. This causes crystals to form which are then recovered by filtration, washed, and dried as appropriate.

In a final step, the crystals are thoroughly dried and ground to a suitable powder form. Drying can be carried out in a vacuum oven at temperatures above room temperature, e.g. from about 30° C. up to about 150° C. This drying is continued until all of the solvent and all of the added acid is gone.

The product so formed is a highly pure high melting form of podophyllotoxin. This material is suitable for pharmaceuticals and in the uses for which podophyllotoxin is well known.

The invention will be further illustrated by the following example which gives a step by step practice of a preferred mode for carrying out the present invention. It will be appreciated that this example is provided to illustrate the best mode to practicing the invention but that the numerous steps and conditions included in this process need not all be practiced to fall within the spirit of the present invention.

EXAMPLE

Step I

Crystallization from commercial resin.

A. Heat 7.5L of absolute EtOH to near reflux in a 22L wide-mouth round-bottomed flask equipped with a mechanical stirrer (glass rod/teflon paddle) and heating mantle in fume hood.

B. Add 2.5kg of preweighed resin in portions over several minutes. Check for complete dissolution with 4 mm glass tubing.

C. Add 2.5L benzene with heating and stirring.

D. Slowly add 2.5L of hot 0.6M aqueous acetic acid solution.

E. Allow to stand and cool. Remove from heating mantle when cool enough to safely do so, but as soon as possible.

F. When cooled to room temperature, place in refrigerator overnight.

G. Filter, using 2L of chilled EtOH/Et$_2$O/H$_2$O (3:1:1/3) as wash and rinse liquid. Combine this liquid with filtrate.

H. Wash collected solid (Crop 1) with 3L of Et$_2$O in several portions. Do not combine with above filtrate.

I. Cool the filtrate from G. overnight.

J. Filter the 2nd crop of crystal obtained in I. washing and rinsing with 800 mL of EtOH/Et$_2$O/H$_2$O (3:1:1/3). Finally, wash with 1L Et$_2$O. (Discard all filtrates).

K. Vacuum dry (room temperature) Crop 1 and Crop 2 separately, then weigh.

Yield: Crop 1 : 626g

Crop 2 : 285g.

Step II.

Adsorbtive filtration from $Al_2O_3$

A. Crops 1 and 2 (910g) are charged to a 5 gallon carboxy with overhead-stirrer, followed by 227 mL acetone and 9.1L $CH_2Cl_2$.

B. After stirring to dissolve the crystals, 1820g of neutral alumina is added in portions over ½ hour.

C. A sample of solution is analyzed by HPLC and further $Al_2O_3$ added as needed to reduce the level of measureable impurities below the integrator's threshold using standardized conditions. Total weight of alumina used: 2300g.

D. After allowing the alumina to settle, the solution is filtered and the alumina washed in 2 portions with 3.4L 80/20 $CH_2Cl_2$/acetone, The washes are combined with filtrate.

E. The solution obtained in D. is allowed to stand overnight to facilitate settling of a very fine, difficultly filterable precipitate. The bulk of the solution is decanted. The balance is gravity filtered through a double layer of fluted filter paper and the combined solutions reduced on the rotovap (50° C. and vacuum).

F. Evaporation of the solvent is continued until the residue is a dough weighing about twice its dry weight.

G. While the residue is still warm, 0.6L of acetone is added to dissolve the solid and 1.6L of $Et_2O$ is added with hand swirling to form a cloudy solution, which is then let stand in the refrigerator overnight.

H. The solid obtained is broken up and transferred as quickly as possible along with the supernatant to a fritted glass vacuum filter funnel, any remaining solid is rinsed into the funnel quickly with ether, and the solids are sucked dry while lumps are crushed.

I. The above solids are resuspended twice in two 900 mL portions of ether and sucked dry.

J. The filtrate and washings are combined, the solvent removed and the residue weighed and analyzed by HPLC in order to evaluate the potential for a second crop.

K. The solid from I. is vacuum dried in a desiccator at room temperature overnight or longer.

Step III

Recrystallization from ethanol/$H_2O$

A. After making sure all lumps are broken up, the solid (388g) from Step II is transferred to a preweighed 4L Erlenmeyer flask containing a suitable teflon stirring bar. After reweighing, ethanol (1160 mL) is added, followed by 43mL of distilled $H_2O$ and 7mL of acetic acid.

B. The mixture is heated (do not boil), stirring on a suitable size hot plate/stirrer until a clear, homogeneous solution results. If needed, the solution can be filtered through a plug of glass wool into another 4L Erlemeyer flask.

C. To the above clear, hot solution is added slowly with adequate stirring 388mL of preheated (to near boiling) 0.1M acetic acid in distilled water.

D. The teflon bar is removed from the solution. The solution is covered with parafilm and allowed to stand at room temperature in the dark until the solution is at ambient temperature. Then place the flask in a −40° C. bath for 24 hours.

E. The cold solution is then filtered, the crystals being collected in a sintered glass funnel and washed with approximately 500mL of 50% ethanol/ $H_2O$.

F. The crystals are placed in a crystallizing dish and vacuum dried in a desiccator for approximately 24 hours. Yield: 402g.

Step IV

The final vacuum dehydration

A. The above solid (400g) is ground to a fine powder in portions with a mortar and pestle. The powder is then spread evenly in a shallow pyrex dish and placed in a vacuum oven and heated at 110°–120° C. for 12–18 hours. The solid is now reground via mortar and pestle, spread evenly in the pyrex dish, and placed back in the oven at 110°–120° C. for 12–18 hours. The pressure is maintained at approximately 2–5 mm of Hg by bleeding nitrogen. The total vacuum oven treatment time (24 hour minimum) for Step A is determined by the absence of the obvious odor of acetic acid in the product.

B. After cooling, the solid is reground a final time and then bottled. Yield: 355g.

What is claimed is:

1. In a process for purifying podophyllotoxin from an impure solution in a solvent comprising an aliphatic halohydrocarbon wherein the podophyllotoxin is recovered as a solid from the solution, the improvement comprising suspending a high surface area solid inorganic adsorbent with the impure solution to adsorb impurities and removing the solid adsorbent and then recovering the podophyllotoxin as a purified material.

2. The improved process of claim 1 wherein the solid adsorbant is selected from titania, boria and alumina.

3. The improved process of claim 2 wherein the said adsorbant is alumina.

4. The improved process of claim 2 wherein the solvent additionally comprises a polar aprotic cosolvent.

5. The improved process of claim 2 wherein the polar aprotic cosolvent is a ketone.

6. The improved process of claim 2 wherein the polar aprotic cosolvent is acetone.

7. The improved process of claim 2 wherein the polar aprotic cosolvent is an ester.

8. The improved process of claim 2 wherein the polar aprotic cosolvent is an amide.

9. The improved process of claim 2 wherein the solid adsorbant is neutral alumina.

10. The improved process of claim 2 wherein the solid adsorbant is acidic alumina.

11. The improved process of claim 2 wherein the solid adsorbant is mildly basic alumina.

12. A process for isolating podophyllotoxin from podophyllum resin comprising:
 a. dissolving podophyllum resin in an organic solvent to yield an impure solution,
 b. adding a cosolvent to the impure solution to cause precipitation of a first stage podophyllotoxin product,
 c. recovering the precipitated first stage podophyllotoxin product,
 d. dissolving the first stage podophyllotoxin product in an organic liquid phase comprising an aliphatic halohydrocarbon to yield a first stage podophyllotoxin product solution,
 e. suspending in the first stage podophyllotoxin product solution the solid phase to yield a second stage solution of purified podophyllotoxin,
 f. recovering purified podophyllotoxin from the second stage solution as a solid.

13. The process of claim 12 wherein in step e. the high surface area solid is suspended in the first stage podophyllotoxin product solution.

14. The process of claim 12 wherein the high surface area solid is a refractory oxide.

15. The process of claim 14 wherein the refractory oxide is selected from boria, titania and alumina.

16. The process of claim 15 wherein the refractory oxide is alumina.

17. The process of claim 16 wherein the alumina is neutral alumina.

18. The process of claim 16 wherein the alumina is acidic alumina.

19. The process of claim 16 wherein the alumina is mildly basic alumina.

20. The process of claim 16 wherein in step a. the organic solvent comprises a lower alcohol.

21. The process of claim 16 wherein in step b. the cosolvent comprises a nonpolar organic liquid plus water.

22. The process of claim 21 wherein in step b. an acid is present.

23. The process of claim 16 wherein in step d. the organic liquid phase comprises halohydrocarbon liquid plus polar aprotic liquid.

24. The process of claim 23 wherein in step d. the organic liquid phase comprises $CH_2Cl_2$ and acetone.

25. The process of claim 16 comprising the additional steps of
   g. dissolving the purified solid podophyllotoxin in a solvent to give a third stage solution, and
   h. recovering pure podophyllotoxin as a recrystallized solid from the third stage solution.

* * * * *